United States Patent
Schara et al.

(10) Patent No.: US 7,134,992 B2
(45) Date of Patent: Nov. 14, 2006

(54) GRAVITY REFERENCED ENDOSCOPIC IMAGE ORIENTATION

(75) Inventors: Nathan Jon Schara, Pasadena, CA (US); Hans David Hoeg, Arcadia, CA (US); Eric Lawrence Hale, South Pasadena, CA (US)

(73) Assignee: Karl Storz Development Corp., Goleta, CA (US)

( * ) Notice: Subject to any disclaimer, the term of this patent is extended or adjusted under 35 U.S.C. 154(b) by 387 days.

(21) Appl. No.: 10/754,130

(22) Filed: Jan. 9, 2004

(65) Prior Publication Data

US 2005/0154260 A1    Jul. 14, 2005

(51) Int. Cl.
*A61B 1/04* (2006.01)
(52) U.S. Cl. ............... 600/118; 600/173; 600/117
(58) Field of Classification Search ........... 600/117, 600/118, 109, 112, 173; 348/65, 74; 382/289
See application file for complete search history.

(56) References Cited

U.S. PATENT DOCUMENTS 5,899,851 A * 5/1999 Koninckx ............... 600/117
6,097,423 A * 8/2000 Mattsson-Boze et al. ..... 348/65
6,464,631 B1 * 10/2002 Girke et al. ............... 600/109
6,471,637 B1 * 10/2002 Green et al. ............... 600/109
2005/0020883 A1 * 1/2005 Chatenever et al. ........ 600/173

FOREIGN PATENT DOCUMENTS

JP      403118019 A   *   5/1991
JP      410262921 A   *   10/1998

* cited by examiner

*Primary Examiner*—John P. Leubecker
(74) *Attorney, Agent, or Firm*—St. Onge Steward Johnston & Reens LLC

(57) ABSTRACT

A method is disclosed in for presenting an endoscopic image in an upright orientation. An electronic rotation pick-up means is fixed to the housing of an endoscope. The electronic rotation pick-up means produces signals indicating rotations of the endoscope. A microprocessor uses these signals to calculate a necessary amount of rotational correction for the endoscopic view orientation. The calculation includes factors to account for endoscope roll, endoscope pitch, and endoscope viewing direction. An image rotator rotates the endoscopic image by the calculated correction amount. The rotated image is displayed on a video display device.

25 Claims, 3 Drawing Sheets

GRAVITY REFERENCED ENDOSCOPIC IMAGE ORIENTATION

CROSS-REFERENCE TO RELATED APPLICATIONS

Not Applicable

STATEMENT REGARDING FEDERALLY SPONSORED RESEARCH

Not Applicable

FIELD OF THE INVENTION

The present invention relates to endoscopes, and in particular those in which the rotational orientation of the endoscopic image as viewed on a screen is presented in its actual relationship to the viewer's reference frame.

BACKGROUND OF THE INVENTION

An endoscope is an elongated tubular structure which is inserted into body cavities to examine them. The endoscope includes a telescope with an objective lens at its distal end. The telescope usually includes an image-forwarding system. In rigid endoscopes it is a series of spaced-apart lenses. In flexible endoscopes it is a bundle of tiny optical fibers assembled coherently to forward the image. Some endoscopes include a camera means, such as a CCD or CMOS image sensor, in the distal portion and forward the image electronically. This invention is applicable to all types of image forwarding systems.

Many endoscopes view only directly forward. Others feature fixed or movable reflectors in the distal portion to allow off-axis viewing. Some, most commonly flexible types, feature actuated bending portions at the distal end. This invention is applicable to all types of axial, non-axial, and variable direction of view endoscopes.

At the proximal end of the image-forwarding system, some endoscopes include an ocular lens which creates a virtual image for direct human visualization. Often a camera means, such as a CCD or CMOS chip, is connected to the endoscope. It receives the image and produces a signal for a video display. Some endoscopes have a camera means built directly into the endoscope.

While surgeons can, and often do, look directly into the endoscope through an ocular lens, it has become more common for them to use an attached video camera and observe an image on a video screen. In a surgical or diagnostic procedure, the surgeon manipulates the endoscope. He may cause it to pitch about a lateral axis or roll about a longitudinal axis. As these manipulations occur to an endoscope with an attached camera, the camera faithfully relates what it sees, with its own upright axis displayed as the upright axis of the image on the display. This often results in rotation of the viewed image.

That is the very problem. When the image is displayed on the screen and the endoscope is manipulated, it is as though the surgeon must tilt his head to follow the rotating image. However, the surgeon is standing up, and the rotating image is distracting to him. What he really wants to see on the screen is an image that is oriented the same as he would see it if he were inside, standing up, with the same upright orientation.

A solution to this problem is proposed in U.S. Pat. No. 5,307,804 to Bonnet (1994), which is incorporated herein by reference in its entirety. An object of this invention was to maintain the orientation of an endoscopic image without the use of electronic sensing and positioning devices. A pendulum fixed to a camera is rotatably attached to an endoscope. The pendulum maintains an orientation with respect to gravity around the endoscope longitudinal axis. As the endoscope rotates, the pendulum causes the camera to rotate in the opposite direction relative to the endoscope. This is intended to maintain the image in a proper orientation.

An endoscope with rotational orientation correction is also suggested in U.S. Pat. No. 5,899,851 to Koninckx (1999), which is incorporated herein by reference in its entirety. An electronic rotation pick-up means responsive to gravity senses rotation of a camera around the endoscope longitudinal axis. An image rotator rotates the camera image according to the rotation signal from the rotation pick-up means.

Another endoscope and camera system with rotational orientation correction is disclosed in U.S. Pat. No. 6,097,423 to Mattsson-Boze, et al. (2000), which is incorporated herein by reference in its entirety. Electronic sensing and positioning devices combine to sense and correct the rotation of a camera rotatably attached to an endoscope. An accelerometer fixed to the camera serves as an electronic rotation pick-up means responsive to gravity. A motor rotates the camera according to signals from the accelerometer. This accelerometer and motor system is functionally equivalent to the pendulum described by Bonnet. While the pendulum relies on the force of gravity to rotate, the small accelerometer sensitively measures gravity and the motor rotates the assembly accordingly. The system can therefore be thought of as an electro mechanical pendulum. Mattsson-Boze also recognizes rotation of the image by electronic manipulation to correct the image orientation, but actively discourages this practice for several reasons.

U.S. Pat. No. 6,471,637 to Green, et al. (2002), which is incorporated herein by reference in its entirety, discloses the same apparatus as disclosed in Mattsson-Boze, and suggests two alternative methods for image rotation. In the first method, an optical image rotator is used instead of a rotating camera. In the second method, electronic manipulation is used to correct the image orientation. Also, one or more gyroscopes are suggested as alternative electronic rotation pick-up means.

U.S. patent application Ser. No. 10/093,650 by Chatenever, et al. (2002), which is incorporated herein by reference in its entirety, discloses the same apparatus as disclosed in Mattsson-Boze and in Green, and suggests two alternative methods for electronic rotation pick-up. In the first method, image analysis is used to compute a rotational signal. In the second method, a machine vision system is used to compute a rotation signal.

All of the above solutions compensate only for roll about the longitudinal axis, and provide a rotationally corrected image for axial viewing endoscopes. They also provide an approximation of the correct orientation for slightly oblique viewing endoscopes held near horizontal. None of the above disclosures suggest a solution that works for significantly oblique, side, or retro viewing endoscopes.

Oblique, side, or retro viewing endoscopes require a solution that takes into account the off-axis viewing direction and the endoscope pitch. Variable direction-of-view endoscopes further complicate the situation.

It is an object of this invention to maintain the proper upright orientation (with respect to the viewer) of a viewed image from an endoscope. It is an additional object of this invention to be applicable to any axial, oblique, side, or retro viewing endoscope as well as any endoscope with a variable direction of view.

BRIEF SUMMARY OF THE INVENTION

According to a feature of this invention an electronic rotation pick-up means is fixed to the housing of an endoscope. The electronic rotation pick-up means produces signals indicating rotations of the endoscope. A microprocessor uses these signals to calculate a necessary amount of rotational correction for the endoscopic view orientation. The calculation includes factors to account for endoscope roll, endoscope pitch, and endoscope viewing direction. An image rotator rotates the endoscopic image by the calculated correction amount. The rotated image is displayed on a video display device. With this arrangement the view presented by the video display will always be "upright", as though viewed by a surgeon standing or sitting in an upright position.

What is claimed is a method for maintaining the proper upright orientation (with respect to the viewer) of an image from an endoscope comprising calculating an image orientation correction, wherein said calculating comprises accounting for the effects on image orientation caused by endoscope pitch, endoscope roll, and endoscope direction of view; rotating said image by said orientation correction; and presenting said image as corrected by said rotating.

DETAILED DESCRIPTION OF THE INVENTION

Figure 1:
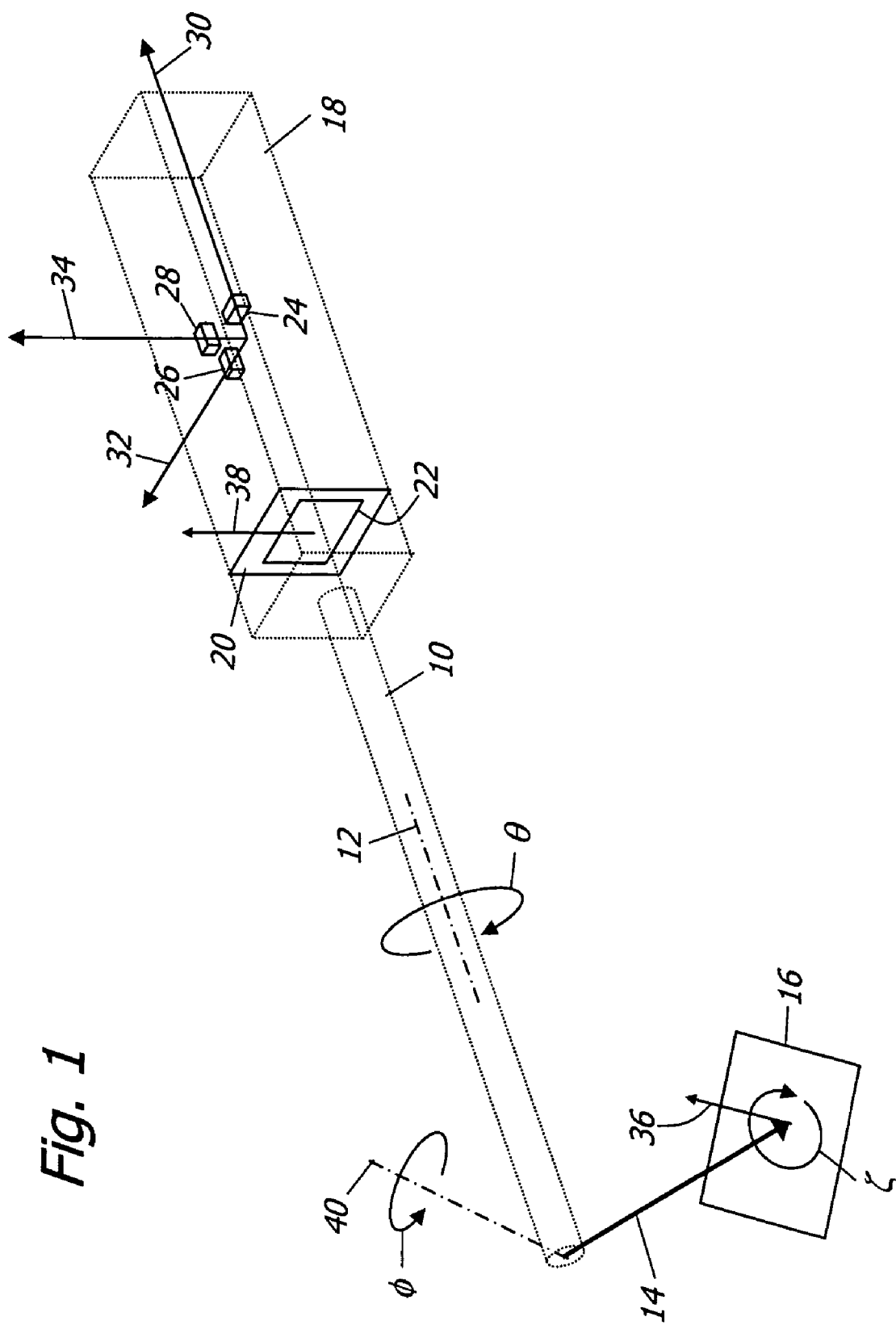
FIG. 1 is a schematic view of an endoscope useful with this invention.

FIG. 1 schematically shows an endoscope. The endoscope includes a shaft 10 that contains elements that are conventionally provided. The shaft has a longitudinal axis 12.

An objective optical system is provided at the distal end of the shaft to give the endoscope a view vector 14 and a field of view 16. The objective optical system comprises components such as lenses, prisms, reflectors, etc. The objective optical system may be adjustable or mounted adjustably to provide a variable direction of view.

A housing 18 is provided at the proximal end of the shaft 10. An image sensing device or camera 20 is mounted in the housing 18. It is configured to receive images 22 from the objective optical system. The housing 18 encases an electronic microprocessor (not shown) for performing calculations. The microprocessor is in communication with an image rotator (not shown), also contained within the housing.

Image rotation can be accomplished in one or more of three ways: physical rotation of the image sensor; optical rotation of the received image prior to incidence upon the image sensor; and electronic rotation of the image within a processor. The details of these methods are not necessary for an understanding of this invention, but are described in Chatenever and other prior art.

Electronic rotation pick-up means, in the preferred embodiment three accelerometers 24, 26, 28 responsive to gravity, are mounted to the housing 18. Each accelerometer measures a component of gravity along a particular measurement axis. The accelerometers provide pulse-width-modulated signals to the processor which can convert each signal into a gravitational force measurement. Changes in the gravitational force measurements from the accelerometers are related to rotations of the endoscope.

In order to adequately describe the method of the current invention, an appropriate mathematical framework needs to be defined.

The housing 18 has a longitudinal axis 30 and a lateral axis 32 which are horizontal when the housing is in its upright position, and an upright axis 34 which is vertical when the housing is in its upright position. These axes 30, 32, 34 are orthogonal. Each accelerometer axis is aligned with an axis of the housing 18. The first accelerometer 24 measures a component of gravity along the longitudinal axis 30. The second accelerometer 26 measures a component of gravity along the lateral axis 32. The third accelerometer 28 measures a component of gravity along the upright axis 34. The force from the longitudinal accelerometer 24 is Z. The force from the lateral accelerometer 26 is X. The force from the upright accelerometer 28 is Y.

The endoscope has a view vector 14. The camera upright projection 36 is the projection of the default upright axis 38 of the camera 20 through the optics and along the view vector 14.

A view vector pivot axis 40 is defined at the distal end of the endoscope, initially aligned with the housing upright axis 34. The pivot axis 40 may or may not exist in the actual implementation of the endoscope, but is defined as part of the mathematical framework. The pivot axis 40 may be realigned by rotating it about the longitudinal axis 12. The variable theta is used to describe the angle of the pivot axis 40 relative to the upright axis 34 as rotated about the longitudinal axis 12. The variable phi is used to describe the angle of the view vector 14 relative to the longitudinal axis 12 as rotated about the pivot axis 40. The variable zeta is used to describe the angle of the camera upright projection 36 relative to the pivot axis 40 as rotated about the view vector 14. It should be noted that the above parameterization uses ZYZ Euler angles, which are commonly used to describe three dimensional rotations.

For simple oblique, side, or retro viewing endoscopes, the above parameterization variables theta, phi, and zeta will be fixed constants defined for each endoscope. Variable direction of view endoscopes require that one or more of the variables change during operation to reflect the changing direction of view.

Figure 2:
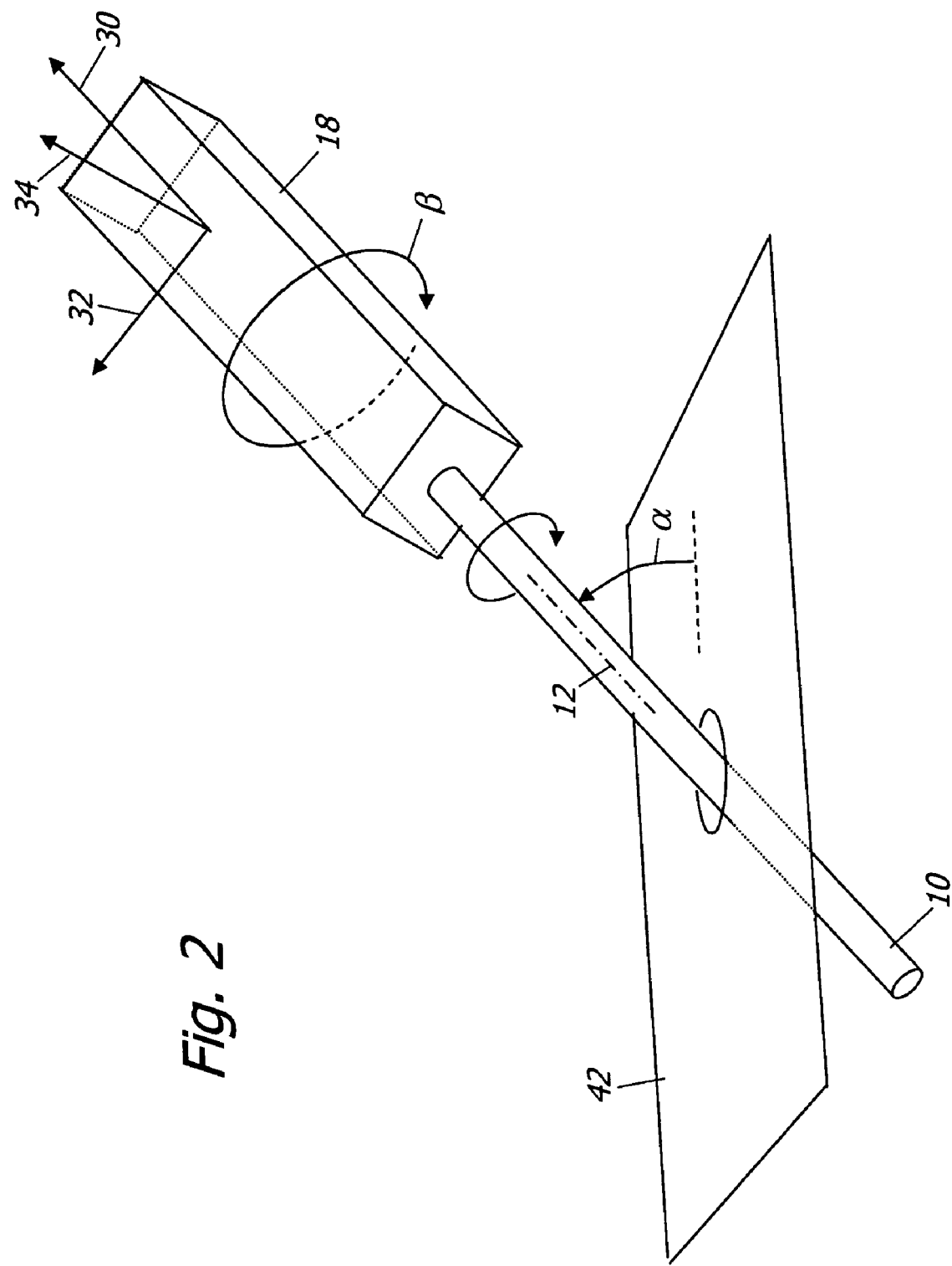
FIG. 2 illustrates endoscope attitude.

During use, the endoscope will be positioned with an attitude as shown in FIG. 2. The attitude is parameterized as pitch and roll. The variable alpha is used to describe the pitch angle of the longitudinal axis 12 relative to horizontal 42. The variable beta is used to describe the roll angle of the endoscope about its longitudinal axis 12. Both pitch and roll may be adjusted during use.

The microprocessor calculates pitch and roll from the accelerometer outputs according to the formulas:

$$\beta = \arctan\frac{X}{Y}$$

$$\alpha = \arctan\frac{Z}{Y/\cos\beta}$$

Figure 3:
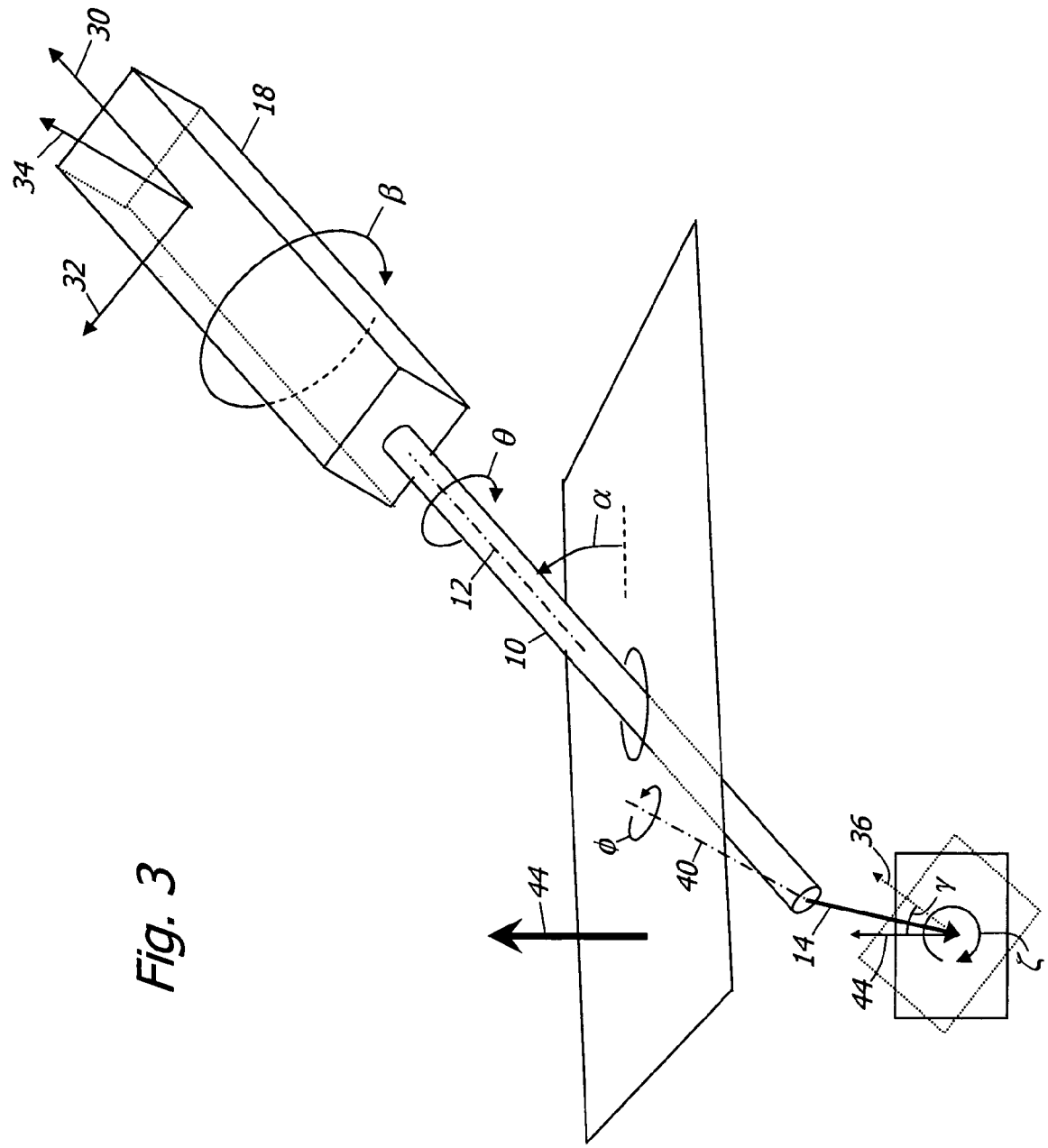
FIG. 3 shows the image orientation correction in accordance with the invention.

As shown if FIG. 3, the camera upright projection 36 is offset from gravity upright 44 by a correction angle. The variable gamma is used to describe the correction angle as a rotation about the view vector 14. The microprocessor calculates gamma according to the formula:

$$\gamma = -\zeta - \arctan\frac{-\sin\alpha\sin\phi + \cos\alpha\cos\phi\sin(\beta + \theta)}{\cos\alpha\cos(\beta + \theta)}$$

The image rotator rotates the image by the angle gamma to align the image in the gravity upright orientation. A video display (not shown) is used to provide the corrected image to the user. The video display may be any device suitable for displaying images from the endoscope.

In an alternative embodiment, one or more gyroscopes can be used as the electronic rotation pick-up means. The gyroscope output is used to determine the attitude of the endoscope. A gyroscope creates a signal representative of a force proportional to the angular displacement relative to its axis of rotation. Methods of determining attitude using gyroscopes are described in Chatenever, but the details of these methods are not necessary for an understanding of this invention.

In a further embodiment of the present invention, a machine vision system is used to compute the attitude of the endoscope. In such a system, the endoscope has thereon or therein at least one signal emitting element which emits some form of energy which is received by a receiver located at some location remote from the endoscope, such is in the ceiling of the operating room, mounted on a tripod or the like, or in a wall. By analyzing the energy received from signal emitting elements, receiver calculates the attitude of the endoscope. Signal emitting elements may themselves generate the energy, such as in the case of light emitting diodes, magnets, or the like, or may comprise reflectors for reflecting energy emitted from some transmitting source located at some location remote from the endoscope, such is in the ceiling of the operating room, mounted on a tripod or the like, or in a wall. Transmitting source thus transmits energy, which is reflected off signal emitting elements, and is received by receiver. The energy may comprise, for example, infrared energy, light in the visual spectrum, magnetic energy, or the like.

The present invention has been described above in terms of a presently preferred embodiment so that an understanding of the present invention can be conveyed. However, there are many alternative arrangements for a method for providing gravity referenced endoscopic image orientation not specifically described herein but with which the present invention is applicable. For example, and alternative mathematical framework describing the endoscope will lead to an alternative formula for the necessary orientation correction. In addition, while the examples were given with respect to endoscopes for use in surgical procedures, the present invention is equally applicable with respect to borescopes or the like for use within various mechanical structures. Therefore, the term "endoscope" as used herein, refers to an endoscope (used for medical procedures) or any similar device such as a borescope, a fiberscope, etc.

This invention is not to be limited by the embodiments shown in the drawings and described in the description, which are given by way of example and not of limitation, but only in accordance with the scope of the appended claims.

We claim:

1. A method for maintaining the proper upright orientation of an image from an endoscope comprising:
   providing an endoscope having a longitudinal axis and a view vector angularly offset from the longitudinal axis at a distal end of the endoscope;
   calculating an image orientation correction, wherein said calculating comprises accounting for the effects on image orientation caused by endoscope pitch, endoscope roll, and the angular offset of the view vector relative to the longitudinal axis;
   rotating said image by said orientation correction; and
   presenting said image as corrected by said rotating.

2. The method of claim 1, wherein said presenting comprises displaying said image on a display device.

3. The method of claim 1, wherein said rotating comprises turning an image pick-up means.

4. The method of claim 1, wherein said rotating comprises turning an optical rotator element.

5. The method of claim 1, wherein said rotating comprises manipulating said image electronically.

6. The method of claim 1, wherein the angular offset of the view vector is fixed.

7. The method of claim 1, wherein the angular offset of the view vector is variable.

8. A method for maintaining the proper upright orientation of an image from an endoscope comprising:
   providing an endoscope having a longitudinal axis and a view vector angularly offset from the longitudinal axis at a distal end of the endoscope;
   calculating an image orientation correction, wherein said calculating comprises accounting for the angle of offset from the endoscope longitudinal axis to the endoscope view vector;
   rotating said image by said orientation correction; and
   presenting said image as corrected by said rotating.

9. The method of claim 8, wherein said presenting comprises displaying said image on a display device.

10. The method of claim 8, wherein said rotating comprises turning an image pick-up means.

11. The method of claim 8, wherein said rotating comprises turning an optical rotator element.

12. The method of claim 8, wherein said rotating comprises manipulating said image electronically.

13. The method of claim 8, wherein the angular offset of the view vector is fixed.

14. The method of claim 8, wherein the angular offset of the view vector is variable.

15. A method for maintaining an upright orientation of images from an endoscope, the method comprising:
   providing an endoscope having a longitudinal axis, an upright axis that is vertical when the endoscope is in an upright position, and a view vector that is angularly offset from the longitudinal axis at a distal end of the endoscope;
   determining a roll angle as the endoscope is rotated about the longitudinal axis;
   determining a pitch angle as the longitudinal axis is inclined relative to horizontal;
   using the roll angle, the pitch angle, and the angular offset of the view vector to calculate a correction angle;
   obtaining an image with the endoscope; and
   rotating the image by the correction angle.

16. The method of claim 15, wherein the steps of determining the roll angle and pitch angle comprise using at least three accelerometers to measure the components of gravity along the upright axis, the longitudinal axis, and a lateral axis substantially orthogonal to the upright and longitudinal axes.

17. The method of claim 16, wherein the step of determining the roll angle comprises calculating the roll angle in accordance with the equation:

$$\beta = \arctan\frac{X}{Y}$$

wherein X is the accelerometer measurement along the lateral axis and Y is the accelerometer measurement along the upright axis.

18. The method of claim 17, wherein the step of determining the pitch angle comprises calculating the pitch angle in accordance with the equation:

$$\alpha = \arctan\frac{Z}{Y/\cos\beta}$$

wherein Z is the accelerometer measurement along the longitudinal axis.

19. The method of claim 18, wherein the step of calculating the correction angle comprises calculating the correction angle in accordance with the equation:

$$\gamma = -\zeta - \arctan\frac{-\sin\alpha\sin\phi + \cos\alpha\cos\phi\sin(\beta+\theta)}{\cos\alpha\cos(\beta+\theta)}$$

wherein $\theta$ is the angle of a view vector pivot axis relative to the upright axis as rotated about the longitudinal axis, $\phi$ is the angle of the view vector relative to the longitudinal axis as rotated about the view vector pivot axis, and $\zeta$ is the angle of the projection of the upright axis relative to the pivot axis as rotated about the view vector.

20. The method of claim 19, wherein at least one of the angle of the view vector pivot axis relative to the upright axis, the angle of the view vector relative to the longitudinal axis, and the angle of the projection of the upright axis relative to the pivot axis is variable.

21. The method of claim 19, wherein the angle of the view vector pivot axis relative to the upright axis, the angle of the view vector relative to the longitudinal axis, and the angle of the projection of the upright axis relative to the pivot axis are constants.

22. The method of claim 15, wherein the step of rotating comprises turning an image pick-up device.

23. The method of claim 15, wherein the step of rotating comprises turning an optical rotator element.

24. The method of claim 15, wherein the step of rotating comprises manipulating said image electronically.

25. The method of claim 15, further comprising the step of displaying the image on a display device.

* * * * *